United States Patent [19]

Hirsch et al.

[11] Patent Number: 4,774,251

[45] Date of Patent: Sep. 27, 1988

[54] METHOD OF INHIBITING AROMATASE

[75] Inventors: Kenneth S. Hirsch, New Palestine; Harold M. Taylor, Indianapolis, both of Ind.

[73] Assignee: Eli Lilly and Company, Indianapolis, Ind.

[21] Appl. No.: 621,584

[22] Filed: Jun. 18, 1984

[51] Int. Cl.$^4$ .................... A61K 31/44; A61K 31/495
[52] U.S. Cl. .................................. 514/357; 514/352; 514/255
[58] Field of Search ................ 424/250, 263; 514/255, 514/352, 357

[56] References Cited

U.S. PATENT DOCUMENTS

| | | | |
|---|---|---|---|
| 2,965,646 | 12/1960 | Gardner et al. | 260/296 |
| 3,784,574 | 1/1974 | Maravetz | 260/347.7 |
| 3,920,651 | 11/1975 | Ecsery et al. | 260/256.4 |
| 3,960,886 | 6/1976 | Schulenberg | 260/326.5 |
| 4,054,655 | 10/1977 | Donald | 424/250 |
| 4,552,960 | 11/1985 | Krumkalns et al. | |

FOREIGN PATENT DOCUMENTS

| | | | |
|---|---|---|---|
| 0000816 | 2/1979 | European Pat. Off. | |
| 7039256 | 5/1967 | Japan | |
| 2056974 | 3/1981 | United Kingdom | 237/20 |

OTHER PUBLICATIONS

Hauser et al., *J. Org. Chem.*, 14, 310 (1949).
Phillips, *J. Am. Chem. Soc.*, 78, 4441 (1956).
Profft, *J. Prakt. Chem.*, 4, 19 (1956).
Chemical Abstracts 51:5074a (1957).
Magnus et al., *J. Am. Chem. Soc.*, 78, 4127 (1956).
Chemical Abstracts 52:2011h (1958).
Chemical Abstracts 60:9239h (1963).
Sengerman et al., *J. Het. Chem.*, 3, 151 (1964).
Matsukawa et al., *J. Pharm. Soc. Japan*, 71, 895 (1951).
Chemical Abstracts 46:8122(c) (1952).
Winternitz et al., *Bull. Soc. Chim. France*, 646 (1952).
Chemical Abstracts 47:12269a (1953).
Gardner et al., *J. Med. Pharm. Chem.*, 3, 461 (1961).
Steinhauser et al., *J. Prakt. Chem.*, 96, 387 (1916).
Chemical Abstracts 10:1639 (1916).
Beahun et al., *J. Org. Chem.*, 26, 4981 (1961).
Gerns et al., *J. Med. Chem.*, 9 (1), 108 (1966).
Clark-Lewis et al., *J. Chem. Soc.*, 5556 (1965).
Derwent Abstract 91247R 12/16/70.
Carter et al, Chemotherapy of Cancer, 2nd Ed. pp. 361, 364 and 365 (1981).

*Primary Examiner*—Allen J. Robinson
*Attorney, Agent, or Firm*—Robert A. Conrad; Leroy Whitaker

[57] ABSTRACT

This invention provides a method of inhibiting aromatase and treating or preventing estrogen-dependent diseases in mammals by administering certain amine derivatives.

16 Claims, No Drawings

METHOD OF INHIBITING AROMATASE

BACKGROUND OF THE INVENTION

Estrogens are synthesized from androgenic steroids. In the biosynthetic pathway for estrogen formation, aromatization is an essential step. It is generally believed that if the aromatase enzyme could be effectively inhibited, a useful treatment for estrogen dependent disorders could be obtained (see *Cancer Research,* Vol. 42, Suppl. 8:3261s (1982)).

Several estrogen dependent diseases exist which could be treated with aromatase inhibitors. These include breast cancer, endometriosis, polycystic ovarian disease, benign breast disease, and endometrial cancer. A beneficial effect of antiestrogens in the treatment of breast cancer has been well established (see *Br. J. Cancer,* 25, 270 (1971)). Two of the known aromatase inhibitors, testolactone and aminoglutethimide, have shown a beneficial effect in treatment of breast cancer. See *Cancer Research,* supra.

Endometriosis is characterized by an abnormal proliferation of the endometrium of the uterus. Since the endometrium is dependent on estradiol for its growth, an inhibitor of estrogen production should stop the progression of the disease.

Benign breast disease, or often called fibrocystic breast disease, appears to be dependent on ovarian steroids. See *Cancer,* 49, 2534 (1982). Aromatase inhibitors have not been tried in this disease, but antiestrogens seem to be of benefit. See *Obstet. Gynecol.,* 54, 80 (1979).

Polycystic ovarian disease is one of the most common causes of infertility in women. The disease appears to result from an abnormality in steroid metabolism, and the major form of therapy in this disease is the antiestrogen, clomiphene. See *Clin. Endocrinol.,* 12, 177 (1980).

It is the purpose of this invention to provide a method of inhibiting the enzyme aromatase in mammals employing certain amine derivatives. The invention thus provides for the treatment or prevention of breast cancer and other estrogen-dependent diseases.

SUMMARY OF THE INVENTION

This invention provides a method of inhibiting aromatase in mammals which comprises administering an aromatase inhibiting amount of a compound of the formula

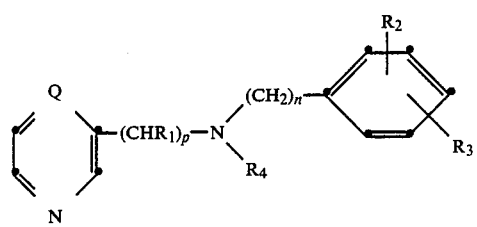

wherein:

Q is CH or N;
p is 0 or 1;
$R_1$ is hydrogen, methyl, ethyl, or

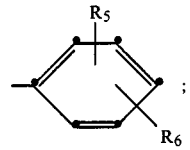

n is 0 or 1;
$R_4$ is hydrogen, $C_1$-$C_8$ alkyl, ($C_2$-$C_4$ alkenyl)methyl, ($C_2$-$C_4$ alkynyl)methyl, or

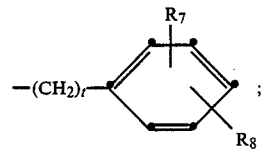

where
$R_2$, $R_3$, $R_5$, $R_6$, $R_7$, and $R_8$ are independently hydrogen, halo, methyl, trifluoromethyl, or methoxy; and
t is 0 or 1,
or a pharmaceutically acceptable salt thereof.

By virtue of their ability to inhibit the enzyme aromatase, the compounds of the above formula are useful in the treatment and prevention of estrogendependent diseases, especially breast cancer, in mammals.

DETAILED DESCRIPTION AND PREFERRED EMBODIMENT

The term "$C_1$-$C_8$ alkyl" refers to branched and straight chain aliphatic radicals of one to eight carbon atoms such as methyl, ethyl, propyl, isopropyl, butyl, tert-butyl, hexyl, octyl, and the like.

The term "$C_2$-$C_4$ alkenyl" refers to straight and branched chain alkenyl radicals of two to four carbon atoms, such as vinyl, propenyl, isopropenyl, butenyl, isobutenyl, and the like. The term "$C_2$-$C_4$ alkynyl" refers to straight and branched chain alkynyl radicals of two to four carbon atoms, such as ethynyl, propargyl, isobutynyl, and the like. The term "halo" refers to fluoro, chloro, bromo, and iodo.

A preferred group of compounds useful in the method of this invention are those wherein:
(a) Q is CH,
(b) p is 1,
(c) $R_1$ is hydrogen or optionally substituted phenyl,
(d) n is 0, and
(e) at least one of $R_2$ and $R_3$ is halo, especially fluoro or chloro, preferably in the para-position.

Most of the compounds used in this invention and methods of making the compounds are disclosed in copending U.S. Patent Application Ser. No. 595,866, filed Apr. 2, 1984. The compounds as disclosed in the patent application are described as being useful as fungicides or intermediates in the preparation of such fungicides. The application does not disclose any utility for use in humans or any utility related to the inhibition of aromatase or estrogen-dependent diseases. Other compounds used in the present application not directly anticipated in the above application can be made in the same way using minor variations in reactants and reaction conditions as will be apparent to one skilled in the art.

The compounds of formula I may be prepared by procedures well known to those skilled in the art. When $R_4$ is other than hydrogen and t is 1, the preferred synthetic process involves alkylating the disubstituted amine starting material or its alkali metal derivative with an appropriately substituted alkyl halide to give a compound of formula I. The scheme for this reaction is as follows:

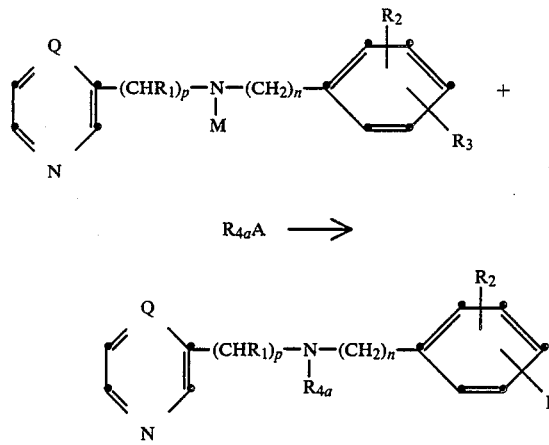

wherein Q, $R_1$, $R_2$, $R_3$, n, and p are as defined above, $R_{4a}$ is $C_1-C_8$ alkyl, ($C_2-C_4$ alkenyl)methyl, ($C_2-C_4$ alkynyl)methyl, or —CH₂—〈aromatic ring with $R_7$, $R_8$〉, A is halogen and M is hydrogen or an alkali metal such as potassium, lithium or sodium. Similarly, when n is 1, the following scheme can be used:

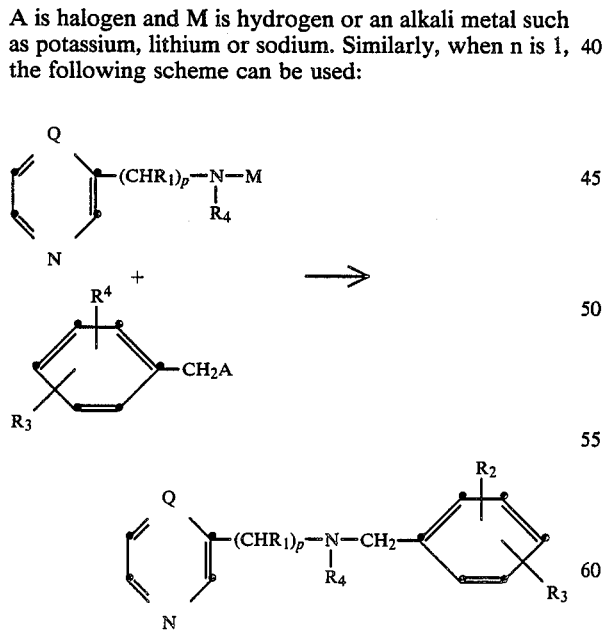

These reactions are performed using standard alkylation techniques which are well known to those skilled in the art. For example, the reaction can be carried out by combining the disubstituted amine with about an equimolar to a slight excess quantity of the alkylating agent in a mutual solvent such as tetrahydrofuran, diethyl ether, dichloromethane, dioxane, dimethylsulfoxide, dimethylformamide, benzene, toluene and the like. A preferred aspect of this reaction involves the addition of a suitable base of sufficient strength to extract the proton on the disubstituted amine starting material. Suitable bases include potassium hydride, lithium hydride, sodium hydride and the like. Typically approximately 1 to 5 equivalents of the base are added to the reaction mixture. The reaction generally is substantially complete after about 2 to about 200 hours when carried out at a temperature of about 20° C. to about 200° C., preferably from about 25° C. to 75° C. The product of the reaction may be isolated by simply removing the reaction solvent, for instance by evaporation under reduced pressure. The residue is then typically dissolved into a water immiscible organic solvent, the solution washed with water and concentrated under vacuum. The amine thus formed may be further purified if needed by any of several routine methods including crystallization from common solvents, chromatography over solid supports such as silica or alumina, and related purification techniques.

Compounds of formula I may be prepared by methods employing known starting materials that are readily available. The disubstituted amines that are employed as starting materials and are also of Formula I ($R_4$ is hydrogen) can be prepared by reacting an appropriately substituted amine with a carbonyl derivative to form a Schiff Base and then reducing the Schiff Base by known procedures, preferably by a palladium on carbon catalyzed hydrogenation reaction or by using sodium borohydride in alcohol. The disubstituted amine starting material may also be prepared by alkylating a primary amine with a halogen derivative again according to standard procedures. The schemes for these reactions are as follows.

When n is 1, the disubstituted amine starting material may be synthesized by the following process:

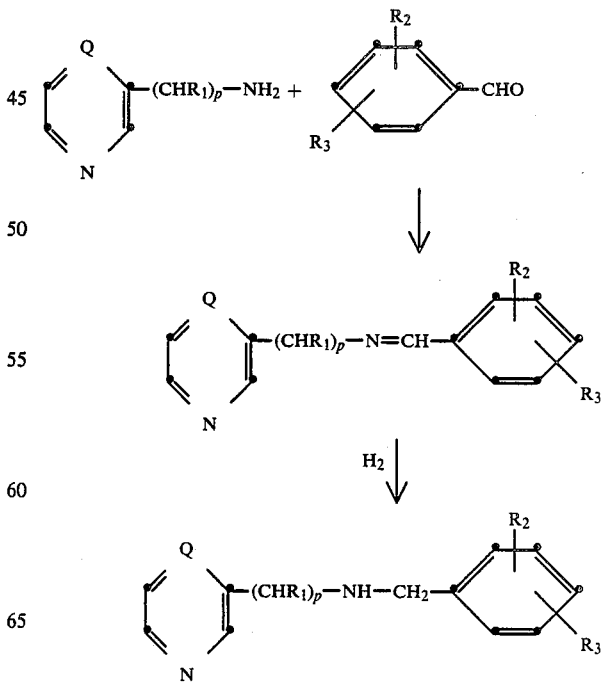

When p is 1, the starting material may be prepared by the following procedures:

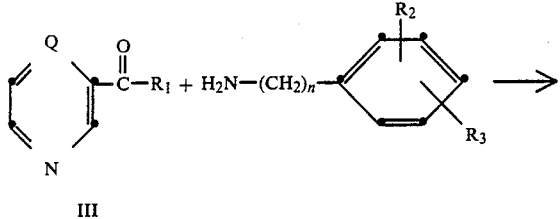

III

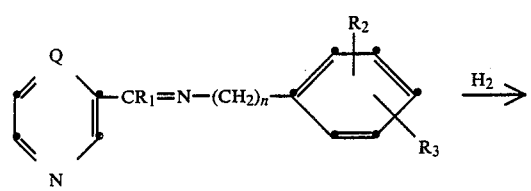

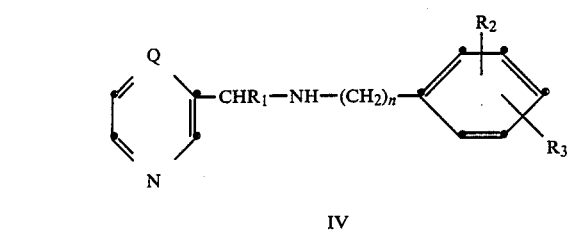

IV

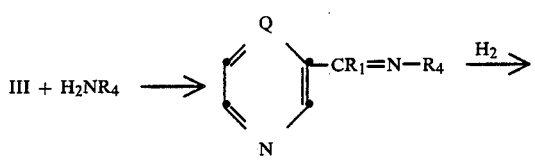

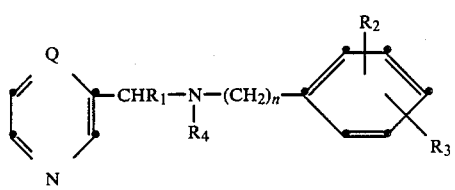

V

The schemes for the alkylation reactions are as follows:

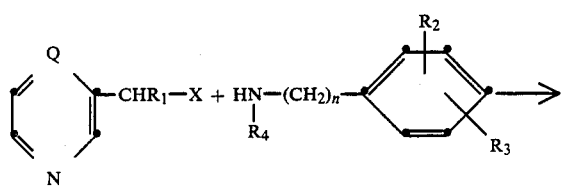

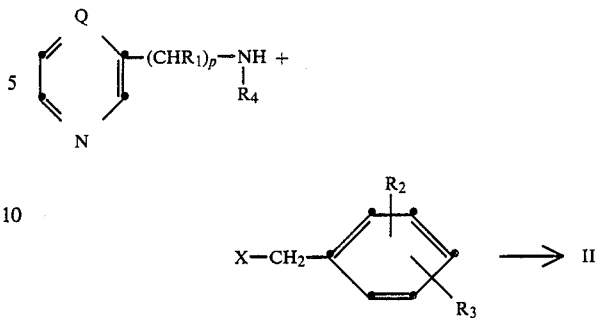

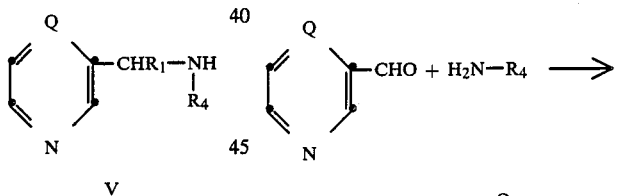

wherein X is a good leaving group such as halogen.

An alternative procedure for preparing disubstituted amine starting materials wherein $R_1$ is other than hydrogen involves combining an aldehyde with an appropriately substituted amine to give the Schiff Base which can then be reacted with a lithium compound to provide the starting material as desired. These reaction schemes are as follows:

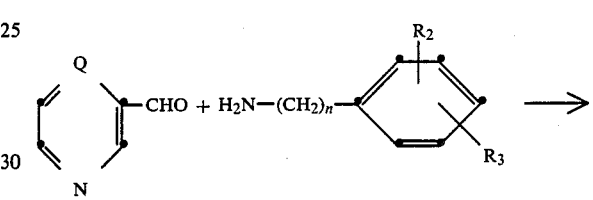

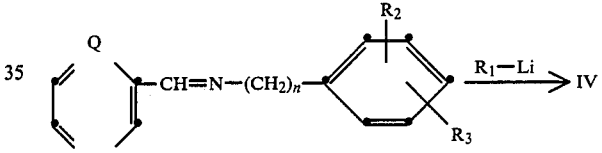

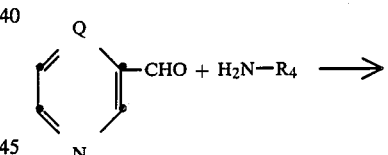

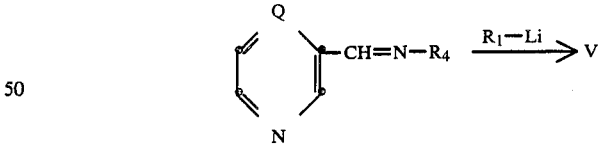

The reaction of the lithium reagent with the imine is typically performed under inert conditions and at a temperature between about −80° C. and 20° C. The reaction is typically complete after about 1 to 24 hours and the product may be isolated by standard procedures.

As will be recognized by those skilled in the art, the compounds of Formula I may contain one or more asymmetric carbon atoms. This invention is not limited to any particular isomer but includes all of the individual stereoisomers of Formula I as well as the mixtures thereof.

The pharmaceutically acceptable acid addition salts of the bases represented by Formula I can be prepared employing those acids of sufficient acidity to form acid addition salts with the weakly basic amine groups. These include both inorganic and organic acids such as hydrochloric, hydrobromic, hydriodic, sulfuric, phosphoric, oxalic, methanesulfonic, benzenesulfonic, p-toluenesulfonic, maleic, and the like acids. Preferred acids for salt formation are the inorganic acids, especially hydrochloric acid.

The compounds used in this invention are useful in preventing or therapeutically treating estrogen-dependent diseases, including breast cancer, in mammals by virtue of their ability to inhibit the enzyme aromatase. The ability to inhibit aromatase was demonstrated by employing a modification of the isolated rat ovarian microsome method of Brodie et al. in *J. Steroid Biochem.*, 7, 787 (1976). In this test system, ovarian microsomes are obtained from rats treated with pregnant mares serum gonadotropin. Test compounds are added to reaction vials containing 0.1 μM 4-androstene-3,17-dione, 100,000 dpm 1,2[$^3$H]-androstenedione, the microsomes and a NADPH generating system. The concentrations of the inhibitors tested ranged between 0.005 and 10 μM. In this assay, aromatization of androstenedione results in the production of [$^3$H]-H$_2$O which is isolated by extracting the samples with chloroform and treating the aqueous phase with charcoal to remove the free steroid. Samples are counted in a liquid scintillation spectrometer and the percent inhibition determined by comparing the results with control samples incubated without inhibitor. Potency is determined based on the concentration of inhibitor in μM required to produce a 50% inhibition of enzyme activity (EC$_{50}$) when the concentration of substrate (androstenedione) is 0.1 μM. The EC$_{50}$'s of certain of the compounds of formula I are summarized in Table 1.

TABLE 1

| Aromatase Inhibition in the Rat Ovarian Microsome Assay | |
|---|---|
| Compound of Formula I | EC$_{50}$* |
| N—butyl-N—[(4-chlorophenyl)-methyl]pyrazinamine | 0.74 |
| N—butyl-N—(2,4-dimethylphenyl)-3-pyridinemethanamine | 0.63 |
| N—(2-butenyl)-N—(2,4-dichlorophenyl)-3-pyridinemethanamine | 0.359 |
| N—butyl-N—(4-chlorophenyl)-α-phenyl-3-pyridinemethanamine | 0.29 |
| N—(2,4-dichlorophenyl)-N—(2-propenyl)-3-pyridinemethanamine | 0.75 |
| N—(2,4-dichlorophenyl)-N—benzyl-3-pyridinemethanamine | 0.31 |
| N—(2,4-dichlorophenyl)-N—(2-propynyl)-3-pyridinemethanamine | 0.165 |
| N—(4-chlorophenyl)-α-methyl-N—benzyl-3-pyridinemethanamine | 1.20 |
| N—(2-chlorophenyl)-α-(4-fluorophenyl)-3-pyridinemethanamine | 0.080 |
| N—(4-chlorophenyl)-N,α-dimethyl-3-pyridinemethanamine | 2.00 |
| N—(2,4-difluorophenyl)-N—benzyl-3-pyridinemethanamine | <0.05 |
| N—(4-chlorophenyl)-N—methyl-α-phenyl-3-pyridinemethanamine | 2.50 |
| N—(2,4-dichlorophenyl)-N—hexyl-3-pyridinemethanamine | 1.20 |
| N—butyl-N—(4-fluorophenyl)-α-methyl-3-pyridinemethanamine | 0.37 |

*Concentration of compound in μM required to achieve 50% inhibition of aromatase activity when substrate concentration is 0.1 μM.

By virtue of their ability to inhibit the enzyme aromatase, the compounds employed in the method of this invention are able to inhibit the synthesis of estrogens in mammals, thereby making the compounds useful in the treatment of estrogen-dependent diseases, such as breast cancer. This in vivo activity was demonstrated in the following test system.

Estrogen Synthesis Inhibition in Rats

Immature female Wistar rats (45–55 grams) were divided into control and test groups of 4–8 animals each. Test compounds were administered for seven days as a component of the diet. Control animals received diet without the test compound. Beginning on the fourth day of the test, all animals treated with the test compound and one half of the control animals were given a subcutaneous injection of 1.0 mg of testosterone propionate in corn oil. The remaining control animals received only an equivalent volume of corn oil. On the seventh day of the test, rats treated with testosterone propionate were injected subcutaneously with 100 μCi of [$^3$H]-testosterone in 50 μl of 3:1 (v/v) saline-ethanol.

After two hours, the animals were killed by decapitation. Uteri were isolated, trimmed of extraneous connective tissue, and weighted. As summarized in Table 2 below, the corn oil treated animals exhibited low uterine weight and represent unstimulated or negative controls. In the control animals treated with testosterone propionate, estrogens produced by aromatization stimulated the uterus resulting in an increase in weight. Compounds which inhibit aromatization produced uterine weights significantly lower than those of the testosterone treated controls.

Ovaries from rats treated with [$^3$H]-testosterone were excised, cleaned of extraneous tissue, and homogenized in 2.5 ml of a 1.0 mM potassium phosphate buffer containing 3.0 mM MgCl$_2$.6H$_2$O, 320 mM sucrose, and 0.25% Triton X-100 (polyethylene glycol p-isooctyl phenyl ether, Rohm and Haas) at pH 6.5. The ovarian steroids were extracted with 1.5 ml of 9:1 (v/v) toluene/ethanol to which had been added 25 to 100 mcg each of unlabelled estradiol, estriol, and estrone, and approximately 1000 dpm of [$^{14}$C]-estradiol. The samples were vortexed, centrifuged at 500×g for 10 minutes, and the organic phase was transferred to a conical vial. Two additional extractions were performed on the residue in the same way. The pooled organic extract were evaporated for subsequent thin-layer chromatography.

Ovarian proteins were precipitated by the addition of 5.0 ml of ethanol to the remaining aqueous phase. After an overnight incubation at 4° C., the samples were centrifuged at 1500×g for 10 minutes. The supernatant was discarded and the pellet was dissolved in 0.3 N potassium hydroxide. Protein was determined according to the method of Bradford, *Analytical Biochemistry*, 72, 248 (1976).

The organic residue from each above extraction was redissolved in 9:1 (v/v) dichloromethane/methanol. The solution of each sample was applied to separate silica gel thin layer chromatography plates which contained a fluorescent indicator. The plates were developed in the first dimension with 160:38:1.5:0.5 (v/v/v/v) dichloromethane/ethyl acetate/methanol/acetic acid to within 3 cm of the top of the plate. After air-drying, the plate was developed in the second dimension with 180:19:1 (v/v/v) dichloromethane/methanol/ammonium hydroxide. The plate was air-dried and viewed under 254 nm UV light.

The visible spots were marked and the plates were sprayed with primulin (0.001% in 4:1 v/v acetone/water) according to the method of Wright, *J. Chromatography*, 59, 220 (1971) which allowed for the identification of additional steroids under 365 nm UV light. The spots were scraped from the plate using a glass wool plugged Pasteur pipet attached to a vacuum line. The steroids were eluted directly into scintillation vials by the addition of 0.2 ml of dichloromethane followed by two washes each of 2.0 ml of methanol. The organic solvent was evaporated and 10.0 ml of scintillation fluid (Beckman Ready Solv-NA) was added to the vials. Samples were analyzed by liquid scintillation spectrometry. Corrections were made based on the recoveries of the [$^{14}$C]-steroid. Steroid concentrations are expressed as femtomoles per milligram protein.

alternatively be dissolved in liquids such as ten percent aqueous glucose solution, isotonic saline, sterile water, or the like, and administered intravenously or by injection. Such solutions can, if desired, by lyophilized and stored in a sterile ampoule ready for reconstitution by the addition of sterile water for ready intramuscular injection.

The compositions are preferably formulated in a unit dosage form, each dosage containing from about 1 to about 500 mg, more usually about 5 to about 300 mg, of the active ingredient. The term "unit dosage form" refers to physically discrete units suitable as unitary

TABLE 2

Effects of Compounds of Formula I on estrogen levels and uterine weight

| Test No. | Compound | Dose* | Animals | Mean Uterine Weight (mg) | Mean Steroid Concentration** | | |
|---|---|---|---|---|---|---|---|
| | | | | | estradiol | estrone | estriol |
| I | N—(2-chlorophenyl)-α-(4-fluorophenyl)-3-pyridine-methanamine | 30 | 4 | 154.3 | 2.67 | 0.47 | 0.51 |
| | | 300 | 5 | 157.4 | 1.64 | 0.31 | 0.37 |
| | Testosterone-treated control | — | 8 | 180.3 | 2.29 | 0.88 | 0.41 |
| | Corn oil control | — | 6 | 66.7+ | — | — | — |
| II | N—(2,4-difluorophenyl)-N—benzyl-3-pyridinemethanamine | 30 | 4 | 196.3 | 0.84 | 0.00 | 0.44 |
| | | 300 | 5 | 171.4 | 0.44 | 0.00 | 0.32 |
| | Testosterone-treated control | — | 8 | 210.4 | 0.78 | 0.41 | 0.17 |
| | Corn oil control | — | 5 | 101.4+ | — | — | — |

*ppm in feed 300 ppm corresponds to approximately 30 mg/kg/day; 30 ppm corresponds to approximately 3 mg/kg/day.
**femtomoles per milligram of protein.
+significantly different from testosterone-treated control, $p < 0.05$.

The compounds may be administered by any number of routes, including the oral, subcutaneous, intramuscular, intravenous, transdermal, and rectal routes. The compounds are usually employed in the form of pharmaceutical compositions. Such compositions are prepared in a manner well known in the pharmaceutical art and comprise at least one active compound of formula I associated with a pharmaceutically acceptable carrier. In making the compositions, the active ingredient will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the composition can be in the form of tablets, pills, powders, lozenges, sachets, cachets, elixirs, emulsions, solutions, syrups, suspensions, aerosols (as a solid or in a liquid medium), ointments containing for example up to 10% by weight of the active compound, soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, tragacanth, gelatin, syrup, methyl cellulose, methyl- and propylhydroxybenzoates, talc, magnesium stearate, water, and mineral oil. The formulations can additionally include lubricating agents, wetting agents, emulsifying and suspending agents, preserving agents, sweetening agents or flavoring agents. The compositions may be formulated so as to provide quick, sustained, or delayed release of the active ingredient after administration to the patient by employing procedures well known in the art.

For oral administration, a compound of Formula I can be admixed with carriers and diluents molded into tablets or enclosed in gelatin capsules. The mixtures can dosages for human subjects and other mammals, each unit containing a predetermined quantity of active material calculated to produce the desired therapeutic effect, in association with a suitable pharmaceutical carrier.

The compounds are effective over a wide dosage range. For example, dosages per day will normally fall within the range of about 0.05 to about 300 mg/kg of body weight. In the treatment of adult humans, the range of about 0.1 to about 50 mg/kg, in single or divided doses, is preferred. However, it will be understood that the amount of the compound actually administered will be determined by a physician, in the light of the relevant circumstances including the condition to be treated, the choice of compound to be administered, the age, weight, and response of the individual patient, the severity of the patient's symptoms, and the chosen route of administration, and therefore the above dosage ranges are not intended to limit the scope of the invention in any way.

In order to more fully illustrate the operation of this invention, the following formulation examples are provided. The examples are illustrative only and are not intended to limit the scope of the invention. The formulations employ as active compounds any of the pharmaceutical compounds of formula I.

EXAMPLE 1

Hard gelatin capsules are prepared using the following ingredients:

| | per capsule |
|---|---|
| N,N—bis(4-chlorophenyl)-pyrazinamine | 250 mg |
| Starch dried | 200 mg |
| Magnesium stearate | 10 mg |
| Total | 460 mg |

The above ingredients are mixed and filled into hard gelatin capsules in 460 mg quantities.

EXAMPLE 2

Capsules each containing 20 mg of medicament are made as follows:

|  | per capsule |
| --- | --- |
| N—(3,4-difluorophenyl)-N—(4-trifluoromethylphenyl)-α-(4-chlorophenyl)-3-pyridinemethanamine | 20 mg |
| Starch | 89 mg |
| Microcrystalline cellulose | 89 mg |
| Magnesium stearate | 2 mg |
| Total | 200 mg |

The active ingredient, cellulose, starch and magnesium stearate are blended, passed through a No. 45 mesh U.S. sieve and filled into hard gelatin capsules in 200 mg quantities.

EXAMPLE 3

Capsules each containing 100 mg of active ingredient are made as follows:

|  | per capsule |
| --- | --- |
| N—t-butyl-N—(4-trifluoromethylbenzyl)pyrazinemethanamine | 100 mg |
| Polyoxyethylenesorbitan monooleate | 50 mcg |
| Starch powder | 250 mg |

The above ingredients are thoroughly mixed and are placed in an empty gelatin capsule.

EXAMPLE 4

Tablets each containing 10 mg of active ingredient are made up as follows:

|  | per tablet |
| --- | --- |
| N—(3-methyl-4-bromophenyl)-N—(2-propynyl)-3-pyridinamine | 10 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 100 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 100 mg.

EXAMPLE 5

A tablet formula is prepared using the ingredients below:

|  | per tablet |
| --- | --- |
| N,N—bis(4-trifluoromethylbenzyl)-α-methyl-3-pyridinemethanamine | 250 mg |
| Cellulose microcrystalline | 400 mg |
| Silicon dioxide fumed | 10 mg |
| Stearic acid | 5 mg |
| Total | 665 mg |

The components are blended and compressed to form tablets each weighing 665 mg.

EXAMPLE 6

Suppositories each containing 25 mg of active ingredient are made as follows:

|  | per suppository |
| --- | --- |
| N—(3-pentenyl)-N—benzylpyrazinamine | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

EXAMPLE 7

Suspensions each containing 5 mg of medicament per 5 ml dose are made as follows:

|  | per 5 ml of suspension |
| --- | --- |
| N—(4-methoxyphenyl)-N—octyl-α-(3,4-dichlorophenyl)-3-pyridinemethanamine | 5 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to | 5 ml |

The medicament is passed through a No. 45 mesh U.S. sieve and mixed with the sodium carboxymethylcellulose and syrup to form a smooth paste. The benzoic acid solution, flavor and color is diluted with some of the water and added, with stirring. Sufficient water is then added to produce the required volume.

EXAMPLE 8

An aerosol solution is prepared containing the following components:

|  | Weight % |
| --- | --- |
| N—(4-chlorophenyl)-N—t-butylpyrazinamine | 0.25 |
| Ethanol | 29.75 |
| Propellant 22 (Chlorodifluoromethane) | 70.00 |

The active compound is mixed with ethanol and the mixture added to a portion of the propellant 22, cooled to −30° C. and transferred to a filling device. The required amount is then fed to a stainless steel container and diluted further with the remaining amount of propellant. The valve units are then fitted to the container.

We claim:

1. A method of inhibiting aromatase in a mammal which comprises administering to said mammal an aromatase inhibiting amount of a compound of the formula

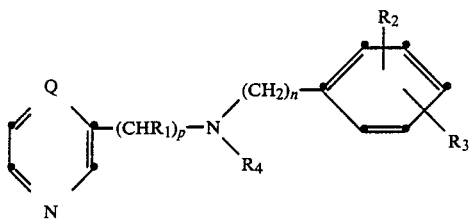

wherein:
Q is CH or N;
p is 0 or 1;
$R_1$ is hydrogen, methyl, ethyl, or

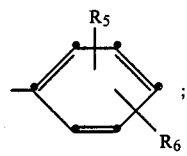

n is 0 or 1;
$R_4$ is hydrogen, $C_1$–$C_8$ alkyl, ($C_2$–$C_4$ alkenyl)methyl, ($C_2$–$C_4$ alkynyl)methyl, or

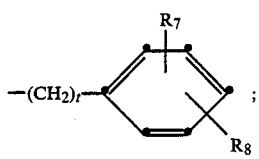

where
$R_2$, $R_3$, $R_5$, $R_6$, $R_7$, and $R_8$ are independently hydrogen, halo, methyl, trifluoromethyl, or methoxy; and
t is 0 or 1,
or a pharmaceutically acceptable salt thereof.

2. The method according to claim 1 employing a compound wherein Q is CH.

3. The method according to claim 2 employing a compound wherein p is 1.

4. The method according to claim 3 employing a compound wherein one of $R_2$ and $R_3$ is chloro or fluoro.

5. The method according to claim 4 employing a compound wherein $R_1$ is hydrogen.

6. The method according to claim 4 employing a compound wherein $R_1$ is optionally substituted phenyl.

7. The method according to claim 5 employing N-(2,4-difluorophenyl)-N-benzyl-3-pyridinemethanamine or a pharmaceutically acceptable salt thereof.

8. The method according to claim 6 employing N-(2-chlorophenyl)-α-(4-fluorophenyl)-3-pyridinemethanamine or a pharmaceutically acceptable salt thereof.

9. A method of treating estrogen-dependent diseases in a mammal which comprises administering to said mammal an effective amount of a compound according to the formula

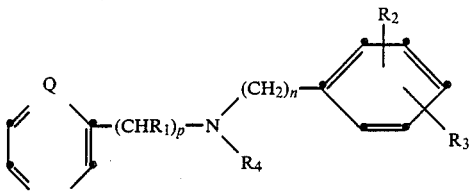

wherein:
Q is CH or N;
p is 0 or 1;
$R_1$ is hydrogen, methyl, ethyl, or

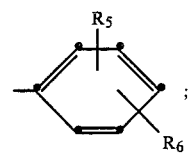

n is 0 or 1;
$R_4$ is hydrogen, $C_1$–$C_8$ alkyl, ($C_2$–$C_4$ alkenyl)methyl, ($C_2$–$C_4$ alkynyl)methyl, or

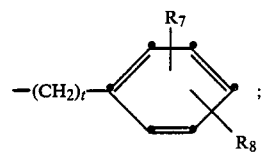

where
$R_2$, $R_3$, $R_5$, $R_6$, $R_7$, and $R_8$ are independently hydrogen, halo, methyl, trifluoromethyl, or methoxy; and
t is 0 or 1,
or a pharmaceutically acceptable salt thereof.

10. The method according to claim 9 employing a compound wherein Q is CH and p is 1.

11. The method according to claim 10 employing a compound wherein one of $R_2$ and $R_3$ is chloro or fluoro.

12. The method according to claim 11 employing N-(2,4-difluorophenyl)-N-benzyl-3-pyridinemethanamine or a pharmaceutically acceptable salt thereof.

13. The method according to claim 11 employing N-(2-chlorophenyl)-α-(4-fluorophenyl)-3-pyridinemethanamine or a pharmaceutically acceptable salt thereof.

14. The method according to claim 9 wherein the estrogen-dependent disease is breast carcinoma cancer.

15. The method according to claim 14 employing a compound wherein Q is CH and p is 1.

16. The method according to claim 15 employing N-(2-chlorophenyl)-α-(4-fluorophenyl)-3-pyridinemethanamine or a pharmaceutically acceptable salt thereof.

* * * * *

UNITED STATES PATENT AND TRADEMARK OFFICE
CERTIFICATE OF CORRECTION

PATENT NO. : 4,774,251
DATED : September 27, 1988
INVENTOR(S) : Kenneth S. Hirsch et al.

It is certified that error appears in the above-identified patent and that said Letters Patent is hereby corrected as shown below:

Column 14, line 57, Claim 14 change "carcinoma cancer." should read --carcinoma.--

Signed and Sealed this

Fourteenth Day of March, 1989

Attest:

DONALD J. QUIGG

Attesting Officer

Commissioner of Patents and Trademarks